(12) United States Patent
Aiken et al.

(10) Patent No.: US 9,249,136 B2
(45) Date of Patent: Feb. 2, 2016

(54) 3H-NAPHTHO [2,1-B] PYRANS AS PHOTOCHROMIC DICHROIC DYES AND OPTICAL ARTICLE CONTAINING THEM

(75) Inventors: Stuart Aiken, Clifton (GB); Jean-Paul Cano, Charenton le Pont (FR); Christopher David Gabbutt, Preston (GB); Bernard Mark Heron, Brough (GB); Tamas Kosa, Hudson, OH (US); Linli Su, Stow, OH (US); Ludmila Sukhomlinova, Kent, OH (US); Bahman Taheri, Shaker Hts., OH (US)

(73) Assignees: Essilor International (Compagnie Generale d'Optique), Charenton-le-Pont (FR); Alphamicron, Incorporated, Kent, OH (US)

( * ) Notice: Subject to any disclaimer, the term of this patent is extended or adjusted under 35 U.S.C. 154(b) by 156 days.

(21) Appl. No.: 12/439,738

(22) PCT Filed: Sep. 6, 2006

(86) PCT No.: PCT/US2006/034507
§ 371 (c)(1),
(2), (4) Date: Jul. 10, 2009

(87) PCT Pub. No.: WO2008/030226
PCT Pub. Date: Mar. 13, 2008

(65) Prior Publication Data
US 2010/0202033 A1 Aug. 12, 2010

(51) Int. Cl.
*G02B 5/23* (2006.01)
*C07D 471/04* (2006.01)
(Continued)

(52) U.S. Cl.
CPC ............ *C07D 471/04* (2013.01); *C07D 311/92* (2013.01); *C07D 405/10* (2013.01); *C07D 455/04* (2013.01)

(58) Field of Classification Search
USPC ................... 359/241, 321; 252/586; 544/150; 546/196, 94; 549/389; 548/525; 524/104, 99, 110
See application file for complete search history.

(56) References Cited

U.S. PATENT DOCUMENTS 5,543,533 A * 8/1996 Allegrini et al. ............ 549/389
5,623,005 A    4/1997 Rickwood et al.
(Continued)

FOREIGN PATENT DOCUMENTS

EP      0629620       12/1994
WO   WO03/080595     10/2003

OTHER PUBLICATIONS

Office Action mailed Apr. 17, 2012 in corresponding Japanese Patent Application No. 2009-527331.
(Continued)

*Primary Examiner* — Bijan Ahvazi
(74) *Attorney, Agent, or Firm* — Occhiuti & Rohlicek LLP

(57) ABSTRACT

A naphthopyran compound represented by the formula (I):

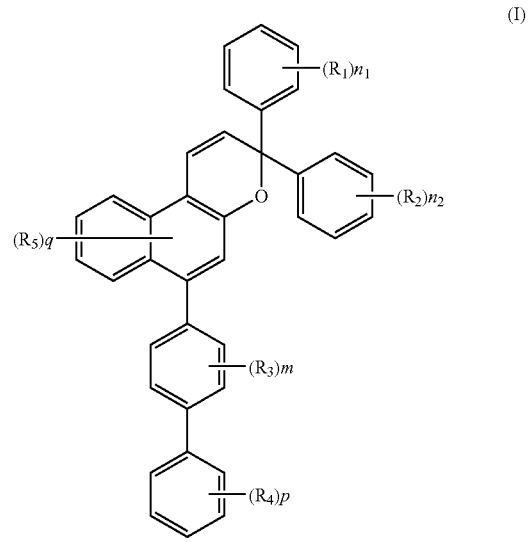

wherein:
$n_1$, $n_2$, p, q is an integer comprised from 0 to 5 inclusive; m is an integer comprised from 0 to 4 inclusive;

$R_1$ and $R_2$ represent a group selected from halogen, $-R_a$, $-OH$, $-OR_a$, $-SH$, $-SR_a$, $-NH_2$, $-NR_aR_{a1}$, $-NR_bR_c$, $-CO-R_a$, and $-CO_2R_{a1}$, wherein $R_a$, $R_{a1}$, $R_b$ and $R_c$, are as defined in the description;

$R_3$ represents a group selected from halogen, $-R_a$, $-OH$, $-OR_a$, $-SH$, $-SR_a$, $-NH_2$, and $-NR_aR_{a1}$;

$R_4$ represents a group selected from halogen, $-R_a$, $-OH$, $-OR_a$, $-SH$, $-SR_a$, $-NH_2$, $-NR_aR_{a1}$, $-CO-R_a$, and $-CO_2R_{a1}$;

$R_5$ represents a group selected from:
halogen, $-R_a$, $-OH$, $-OR_a$, $-SH$, $-SR_a$, $-NH_2$, and $-NR_aR_{a1}$, wherein $R_a$ and $R_{a1}$ are as defined hereinbefore,
or when q is equal to 2, then two $R_5$ together represent further a group $-O-(CH_2)_{q1}-O-$ wherein q1 represents an integer comprised from 1 to 3 inclusive.

20 Claims, No Drawings

(51) Int. Cl.
*C07D 311/92* (2006.01)
*C07D 405/10* (2006.01)
*C07D 455/04* (2006.01)
*G02F 1/03* (2006.01)
*G02F 1/07* (2006.01)
*C07D 401/00* (2006.01)

(56) References Cited

U.S. PATENT DOCUMENTS

| | | | |
|---|---|---|---|
| 5,699,182 A | 12/1997 | Alfekri | 359/321 |
| 6,630,597 B1 * | 10/2003 | Lin et al. | 549/389 |
| 8,703,978 B2 * | 4/2014 | Aiken et al. | 549/389 |
| 2005/0004361 A1 | 1/2005 | Kumar et al. | 544/71 |
| 2005/0096467 A1 | 5/2005 | Mann et al. | 540/596 |
| 2006/0006336 A1 * | 1/2006 | Cano et al. | 250/345 |
| 2010/0039688 A1 * | 2/2010 | Aiken et al. | 359/241 |

OTHER PUBLICATIONS

Opposition as filed Sep. 19, 2012 in corresponding European Patent EP 2 066 650 (Application No. 06790163.7).

Bahadur, Birendra, et al. "Liquid Cryistals—Applications and Uses" vol. 3 *World Scientific publishing Co. Pte Ltd.*. Chapter 11—Dichroic Liquid Crystal Displays (pp. 68-71, 98-105) 1992.

* cited by examiner

3H-NAPHTHO [2,1-B] PYRANS AS PHOTOCHROMIC DICHROIC DYES AND OPTICAL ARTICLE CONTAINING THEM

CROSS-REFERENCE TO RELATED APPLICATIONS

This application is the National Stage of International Application No. PCT/US2006/034507, filed on Sep. 6, 2006, the contents of which are hereby incorporated by reference in their entirety.

TECHNICAL FIELD

The present invention is directed to a group of novel dyes that are both photochromic and dichroic and to the use thereof in optical articles, especially in optical lenses such as ophthalmic lenses.

BACKGROUND ART

Photochromism is a well known physical phenomenon that is observed with certain classes of chemical compounds. A detailed discussion of this phenomenon can be found in "Photochromism: Molecules and Systems", Studies in Organic Chemistry 40, edited by H. Durr and H. Bouas-Laurent, Elsevier, 1990.

A number of substituted 3H-naphtho[2,1-b]pyrans are known to be capable of exerting a reversible photochromic effect as described for example in WO 99/31082, U.S. Pat. No. 6,630,597, U.S. Pat. No. 5,552,090, U.S. Pat. No. 5,520,853, and U.S. Pat. No. 5,623,005. However, none of these 3H-naphtho[2,1-b]pyrans compounds are reported to have dichroic properties.

Passive photochromic devices, i.e. devices containing photochromic dyes whose absorbance depends only from the presence or absence of UV light, typically exhibit rather quick activation (coloration) but it generally takes several minutes or even tens of minutes to revert from the coloured to the bleached state. This slow fading is a severe drawback for the user of photochromic glasses who has to take them off to have clear vision when leaving the sunlight and entering dimmer light conditions.

Therefore, there is a need for photochromic dyes exhibiting not only good photochromic properties, such as high absorption in the coloured state, fast colouring and fading rates, but which also may be capable of dichroism and linear light polarization when in a spatially ordered condition, for example when incorporated into liquid crystals or oriented polymer host materials.

SUMMARY OF THE INVENTION

In light of the foregoing, it is first aspect of the present invention to provide a dye that is both photochromic and dichroic.

It is another aspect of the present invention to provide a naphthopyran compound represented by the formula (I)

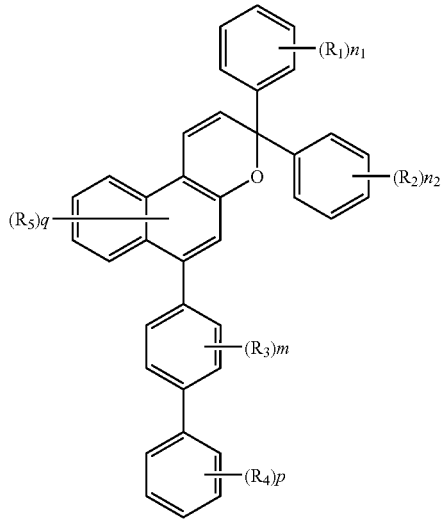

wherein:
$n_1$ is an integer comprised from 0 to 5 inclusive;
$n_2$ is an integer comprised from 0 to 5 inclusive;
p is an integer comprised from 0 to 5 inclusive;
m is an integer comprised from 0 to 4 inclusive;
q is an integer comprised from 0 to 5 inclusive;
$R_1$ and $R_2$, identical or different, independently from each other, represent a group selected from halogen, —$R_a$, —OH, —O$R_a$, —SH, —S$R_a$, —NH$_2$, —N$R_a R_{a1}$, —N$R_b R_c$,
—CO—$R_a$, —O—CO—$R^a$ and —CO$_2 R_{a1}$, wherein:
$R_a$ represents a linear or branched ($C_1$-$C_{18}$) alkyl group or a linear or branched ($C_1$-$C_{18}$) perfluoroalkyl group;
$R_{a1}$ represents a group selected from hydrogen, linear or branched ($C_1$-$C_{18}$) alkyl group and linear or branched ($C_1$-$C_{18}$) perfluoroalkyl group;
$R_b$ and $R_c$,
together and in combination with the nitrogen atom, represent a saturated 5 to 7 membered heterocyclic group which comprises optionally one additional heteroatom selected from O, N and S, and which may be optionally substituted by a group selected from halogen, $R_a$, —OH, —O$R_a$, —NH$_2$, and —N$R_a R_{a1}$, wherein $R_a$ and $R_{a1}$ are as defined hereinbefore;
or together and in combination with the nitrogen atom and the adjacent phenyl group form a heterocyclic group of formula (A):

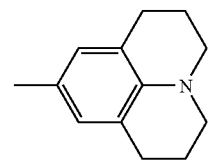

(A)

$R_3$ represents a group selected from halogen, —$R_a$, —OH, —O$R_a$, —SH, —S$R_a$, —NH$_2$, and —N$R_a R_{a1}$, wherein $R_a$ and $R_{a1}$ are as defined hereinbefore;
$R_4$ represents a group selected from halogen, —$R_a$, —OH, —O$R_a$, —SH, —S$R_a$, —NH$_2$, —N$R_a R_{a1}$, —CO—$R_a$, and —CO$_2 R_{a1}$, wherein $R_a$ and $R_{a1}$ are as defined hereinbefore;

$R_5$ represents a group selected from:
halogen, —$R_a$, —OH, —$OR_a$, —SH, —$SR_a$, —$NH_2$, and —$NR_aR_{a1}$, wherein $R_a$ and $R_{a1}$ are as defined hereinbefore, or when q is equal to 2 and then two $R_5$ substituents are located onto two adjacent carbon atoms selected from C-7, C-8, C-9 and C-10 of the naphtho[2,1-b]pyran group, they may further represent together a group —O—$(CH_2)_{q1}$—O— wherein q1 represents an integer comprised from 1 to 3 inclusive.

Yet another aspect of the present invention provides an optical article comprising one or more naphthopyran compounds of the present invention.

BEST MODE FOR CARRYING OUT THE INVENTION

The present invention provides photochromic-dichroic 3H-naphtho[2,1-b]pyrans having a substituted biphenyl group at C-6 of the naphthopyran group.

In one or more embodiments, incorporation of a biphenyl moiety significantly improves dichroic properties of the photochromic dyes in the activated state. The new dye compounds when incorporated into anisotropic host materials such as liquid crystals or oriented polymers will strongly align with the host material molecules and exhibit strong dichroism, i.e. light polarizing, in the coloured state. The new dyes present an order parameter of greater than about 0.6 and excellent solubility in liquid crystal hosts and most of organic solvents.

In certain embodiments, the photochromic dyes of the present invention surprisingly present a very fast fading rate, especially when dissolved in a fluid, mesomorphous or gel host medium. In one or more embodiments, they are able to revert from the coloured to the bleached state in less than five minutes, which constitutes an important advantage over most of the prior art photochromic dyes.

Accordingly, the present invention provides naphthopyran compounds represented by the formula (I)

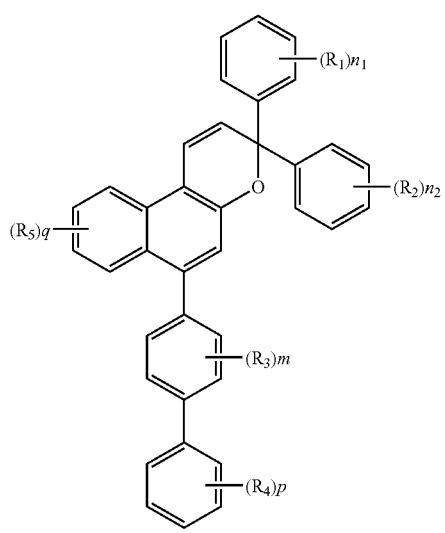

(I)

wherein:
$n_1$ is an integer comprised from 0 to 5 inclusive;
$n_2$ is an integer comprised from 0 to 5 inclusive;
p is an integer comprised from 0 to 5 inclusive;
m is an integer comprised from 0 to 4 inclusive;
q is an integer comprised from 0 to 5 inclusive;
$R_1$ and $R_2$, identical or different, independently from each other, represent a group selected from halogen, —$R_a$, —OH, —$OR_a$, —SH, —$SR_a$, —$NH_2$, —$NR_aR_{a1}$, —$NR_bR_c$,
—CO—$R_a$, —O—CO—$R^a$ and —$CO_2R_{a1}$, wherein:
$R_a$ represents a linear or branched ($C_1$-$C_{18}$) alkyl group or a linear or branched ($C_1$-$C_{18}$) perfluoroalkyl group;
$R_{a1}$ represents a group selected from hydrogen, linear or branched ($C_1$-$C_{18}$) alkyl group and linear or branched ($C_1$-$C_{18}$) perfluoroalkyl group;
$R_b$ and $R_c$,
together and in combination with the nitrogen atom, represent a saturated 5 to 7 membered heterocyclic group which comprises optionally one additional heteroatom selected from O, N and S, and which may be optionally substituted by a group selected from halogen, $R_a$, —OH, —$OR_a$, —$NH_2$, and —$NR_aR_{a1}$, wherein $R_a$ and $R_{a1}$ are as defined hereinbefore;
or together and in combination with the nitrogen atom and the adjacent phenyl group form a heterocyclic group of formula (A):

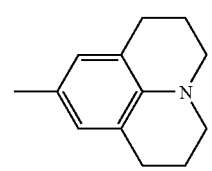

(A)

$R_3$ represents a group selected from halogen, —$R_a$, —OH, —$OR_a$, —SH, —$SR_a$, —$NH_2$, and —$NR_aR_{a1}$, wherein $R_a$ and $R_{a1}$ are as defined hereinbefore;
$R_4$ represents a group selected from halogen, —$R_a$, —OH, —$OR_a$, —SH, —$SR_a$, —$NH_2$, —$NR_aR_{a1}$, —CO—$R_a$, and —$CO_2R_{a1}$, wherein $R_a$ and $R_{a1}$ are as defined hereinbefore;
$R_5$ represents a group selected from:
halogen, —$R_a$, —OH, —$OR_a$, —SH, —$SR_a$, —$NH_2$, and —$NR_aR_{a1}$, wherein $R_a$ and $R_{a1}$ are as defined hereinbefore,
or when q is equal to 2 and then two $R_5$ substituents are located onto two adjacent carbon atoms selected from C-7, C-8, C-9 and C-10 of the naphtho[2,1-b]pyran group, they may further represent together a group —O—$(CH_2)_{q1}$—O— wherein q1 represents an integer comprised from 1 to 3 inclusive.

Preferred naphthopyrans according to the present invention are compounds of formula (I), wherein:
$n_1$ is equal to 0 or 1, and $R_1$ represents a group selected from halogen, —OH and —$OR_a$ located at the para- or ortho-position of the phenyl group, wherein $R_a$ is as defined hereinbefore;
$n_2$ is equal to 1 and $R_2$ represents a group selected from halogen, —OH, —$OR_a$, and —$NR_bR_c$ located at the para-position of the phenyl group, wherein $R_a$, $R_b$ and $R_c$ are as defined hereinbefore;
m is equal to zero;
p is equal to 1 and $R_4$ represents a group selected from —$R_a$, —$OR_a$, and —$NR_aR_{a1}$ located at the para-position of the phenyl group; and q is an integer comprised from 0 to 2 inclusive, and $R_5$ represents a group selected from —OH and —OR$_a$ located on the C-8 and/or C-9 of the naphtho[2,1-b]-pyran group.
Examples of most preferred compounds of formula (I) are the compounds represented by the following formulas (a) to (p):
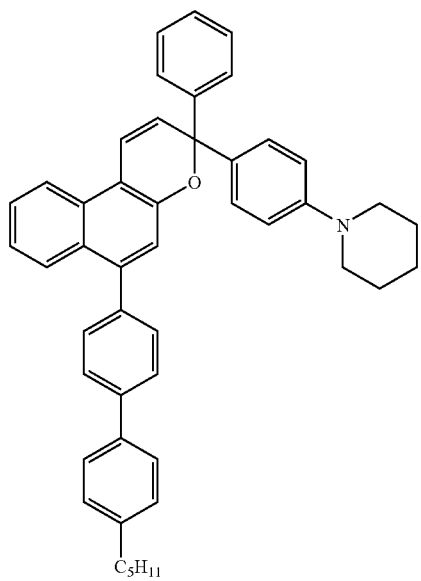
(a)
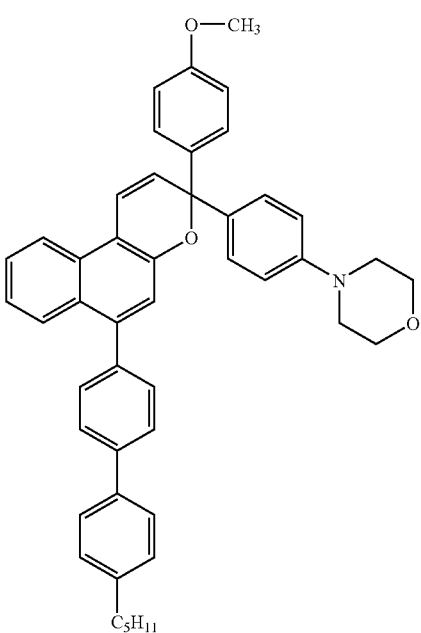
(b)
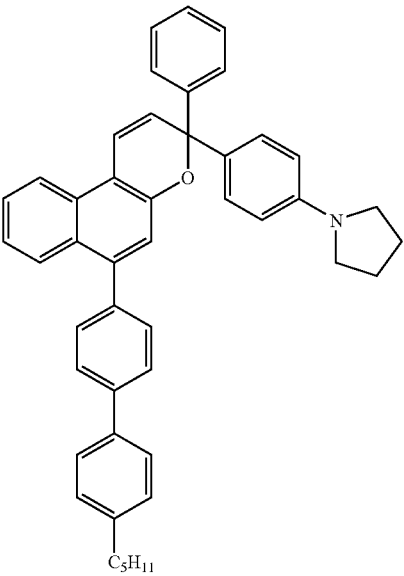
(c)
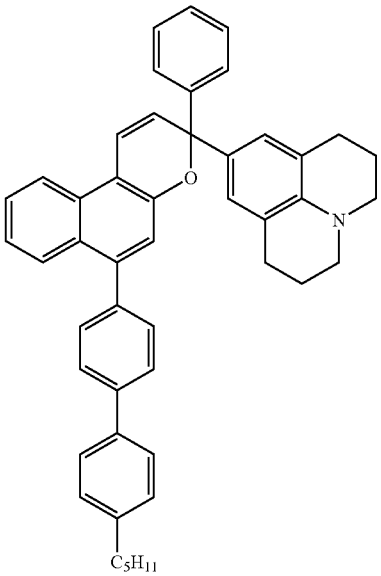
(d)

(e)
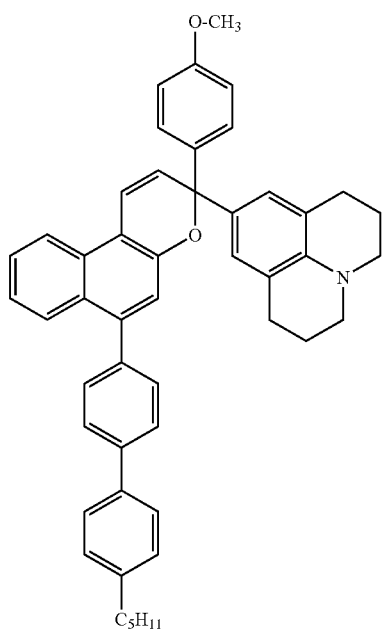
(g)
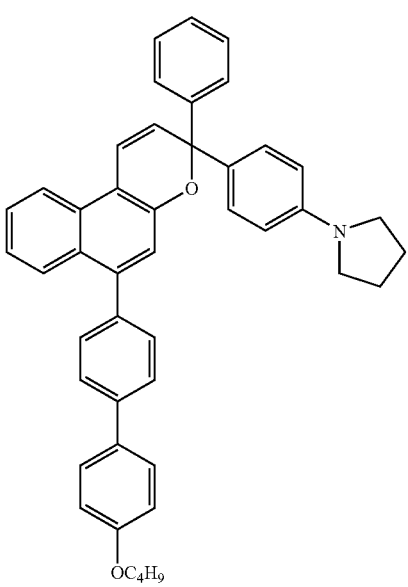
(f)
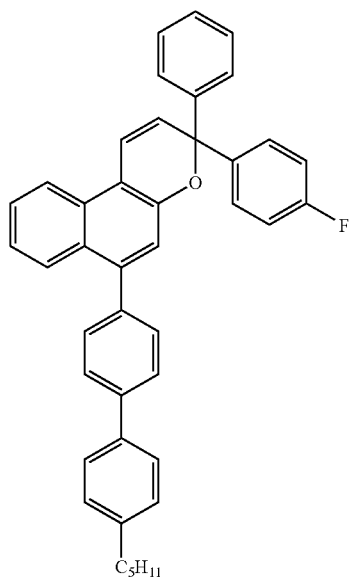
(h)
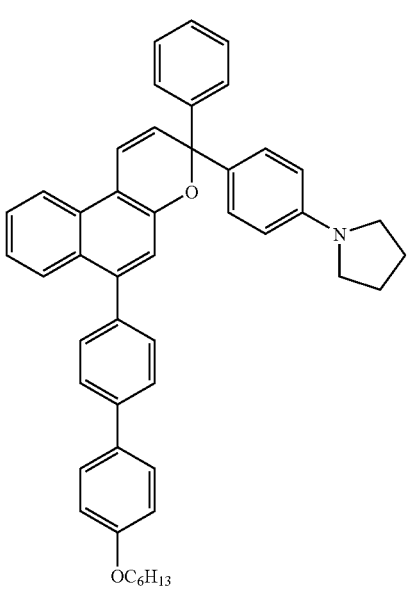

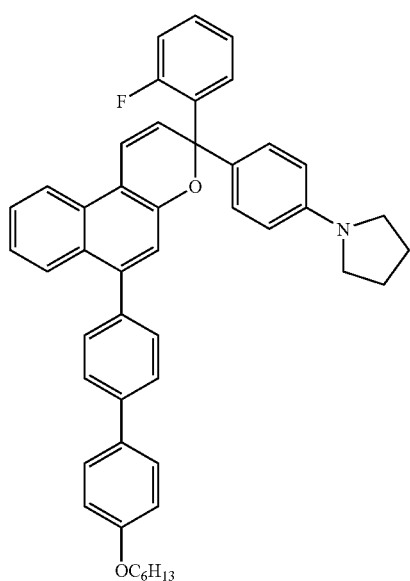
(i)
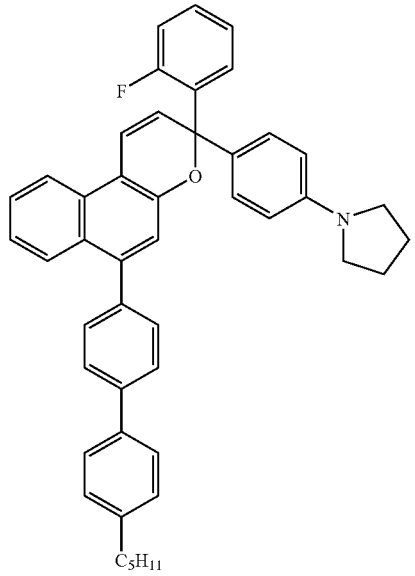
(j)
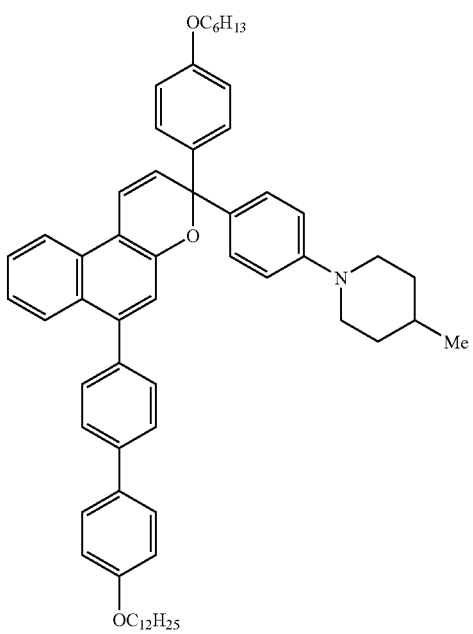
(k)
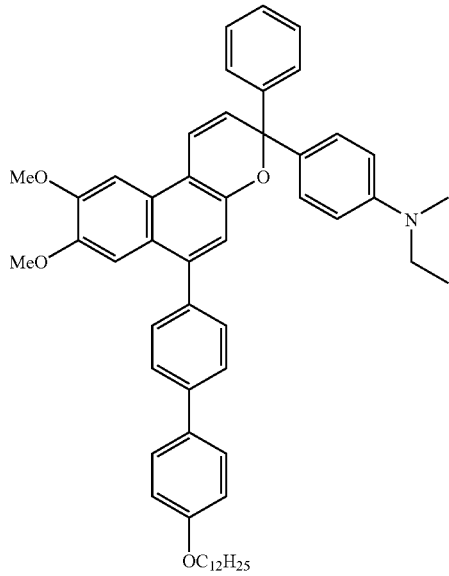
(l)

(m)

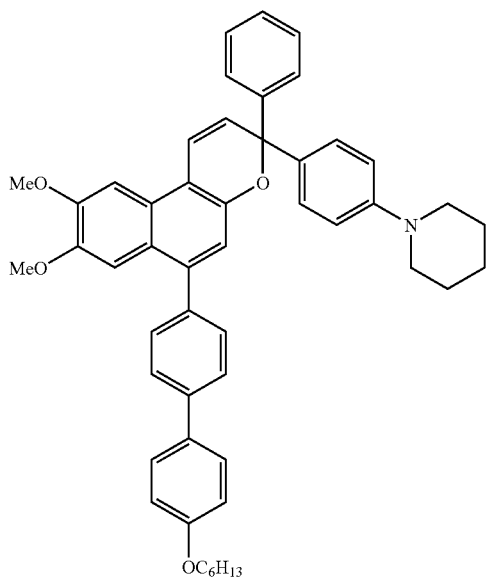

(n)

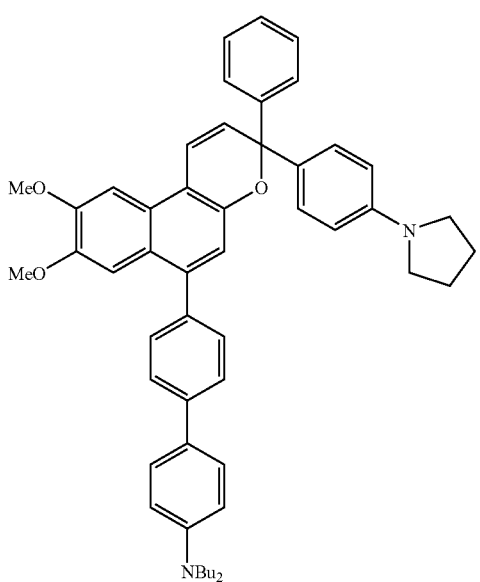

(o)

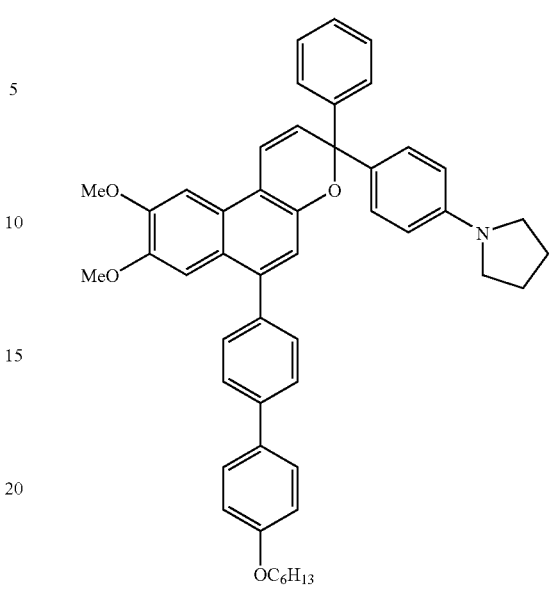

(p)

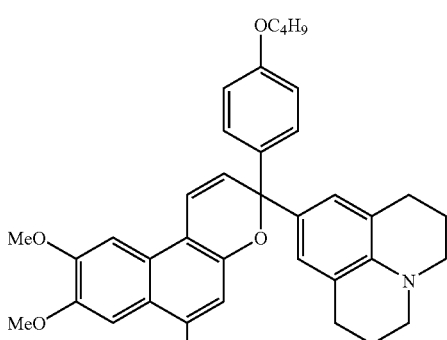

Compounds represented by formula (I) may be prepared according to the following descriptions and reaction schemes:

The requisite naphthols may be prepared as shown in Schemes 1-4. For example, 4-bromo-2-naphthol 1 may be prepared, as shown in Scheme 1, by sequential bromination, diazotisation and reduction of 1-naphthylamine according to the published procedure (M. S. Newman, V. Sankaran and D. Olson, *J. Am. Chem. Soc.,* 1976, 98, 3237), which is hereby incorporated by reference.

1,3-Dihydroxynapthalene is readily available according to the procedure of Meyer and Bloch; (*Org. Synth. Coll. Vol.,* 3, p. 637), hereby incorporated by reference, and may be selectively methylated to give 3-methoxy-1-naphthol in high yield as described in K. H. Bell and L. F. McCaffrey, *Aust. J. Chem.,* 1993, 46, 731, which is hereby incorporated by reference. Subsequent sulfonylation with trifluoromethanesulfonic anhydride provides the trifate 2 in about a 74% yield (Scheme 2), and this procedure is described in S. C. Benson, J. Y. L. Lam, S. M. Menchen, U.S. Pat. No. 5,936,087, hereby incorporated by reference.

Suzuki-Miyaura coupling of 2 with 4'-methoxybiphenyl-4-boronic acid may be employed to give 3, after treatment with excess boron tribromide (Scheme 3). Suzuki-Miyaura coupling is described in A. Suzuki, *J. Organomet. Chem.*, 1999, 576, 147; N. Miyaura, *Top. Curr. Chem.*, 2002, 219, 11, hereby incorporated by reference. 4'-methoxybiphenyl-4-boronic acid is further described in V. Percec, P. Chu and M. Kawasumi, *Macromolecules*, 1994, 27, 4441, hereby incorporated by reference.

The preparation of naphthol 4 may involve an initial Claisen-type condensation of methyl (3,4-dimethoxyphenyl) acetate and 4'-bromoacetophenone mediated by sodium hydride (Scheme 4). Acylation reactions of this type of active CH compound have been reviewed (C. R. Hauser, F. W. Swamer and J. T. Adams, *Org. React.*, 1954, 8, 126; B. R. Davies and P. J. Garratt, *Comprehensive Organic Synthesis*, Pergamon, Oxford, 1991, vol. 2, p. 795, both of which are incorporated by reference). Cyclodehydration of the intermediate 1,3-diketone to 4 may be accomplished under acidic conditions (A. V. Kel'in and Y. Yu. Kozyrkov *Synthesis*, 1998, 729; WO 99/31082, both of which are incorporated by reference).

The preparation of 1,1-diarylprop-2-yn-1-ols 5 from lithium trimethylsilylacetylide and a benzophenone according to Scheme 5 has been documented (e.g. C. D. Gabbutt, J. D. Hepworth, B. M. Heron, S. M. Partington and D. A. Thomas, *Dyes Pigm.*, 2001, 49, 65, which is incorporated by reference).

The preparation of the 6-substituted naphtho[2,1-b]pyrans may be accomplished by the acid catalysed condensation of the appropriate 2-naphthol 1, 3 or 4 and alkynol derivatives 5 as shown in Scheme 6. This route to naphthopyrans has been reviewed (B. Van Gemert, *Organic Photochromic and Thermochromic Compounds Volume 1: Main Photochromic Families*, Ed. J. C. Crano and R. Gugglielmetti, Plenum Press, New York, 1998, p. 111; J. D. Hepworth and B. M. Heron, *Functional Dyes*, Ed. S.-H. Kim, Elsevier, Amsterdam, 2006, p. 85; C. D. Gabbutt, B. M. Heron, A. C. Instone, P. R. Horton, M. B. Hursthouse, *Tetrahedron*, 2005, 61, p. 463, all of which are hereby incorporated by reference).

The bromonaphthopyrans 6 and 8 may serve as substrates for further modification by Suzuki-Miyaura coupling to the appropriate 4'-substituted-4-biphenylboronic acid (prepared as described by e.g. M. R. Friedman, K. J. Toyne, J. W. Goodby and M. Hird, *Liquid Crystals*, 2001, 28, 901, hereby incorporated by reference) and 4-substituted phenylboronic acid to give the 6-(4'-substituted-4-biphenyl)naphtho[2,1-b] pyrans of general structure (I) as illustrated by examples (a)-(j) and (m)-(p) respectively. Alternatively, the naphthopyran 7 may be alkylated as illustrated by examples (k) and (l). These three general sequences are shown in Scheme 7. More specifically, the preparation of Example (1) is outlined in Scheme 8. Noteworthy is the assembly of the 6-(4'-hydroxy-4-biphenyl) moiety via Suzuki-Miyaura coupling of a bromonaphthopyran derivative 8 to readily available 4-(triisopropylsilyloxy)phenylboronic acid (D. J. Aitken, S. Faure and S. S. Roche, *Tetrahedron Lett.*, 2003, 44, 8827, see also M. E. Hart et al. *J. Med. Chem.*, 2006, 49, 1101, both of which are hereby incorporated by reference).

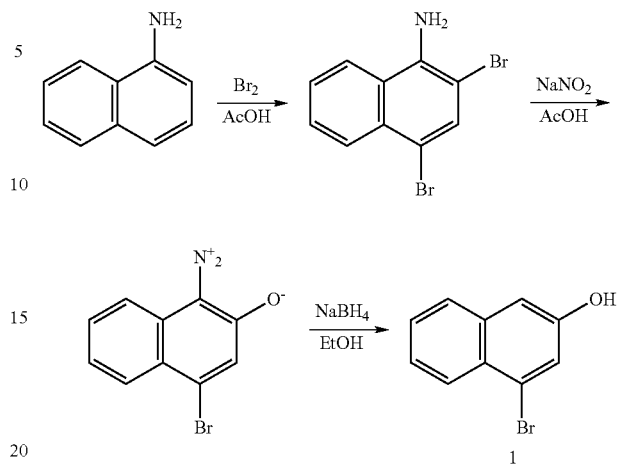

Scheme 1

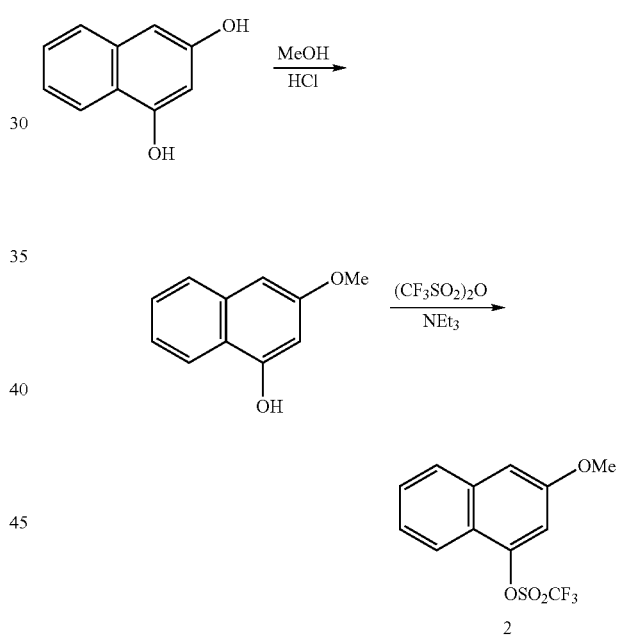

Scheme 2

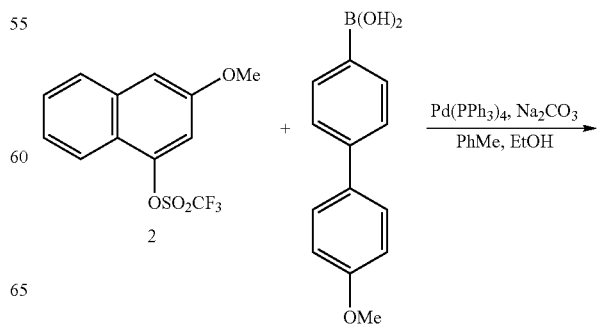

Scheme 3

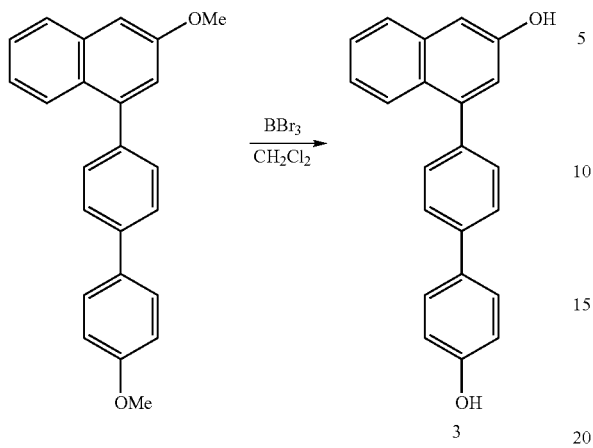
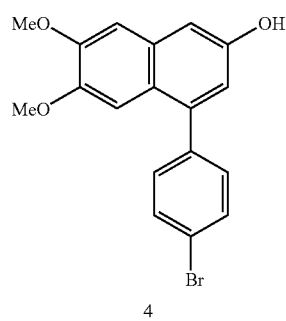
Scheme 4
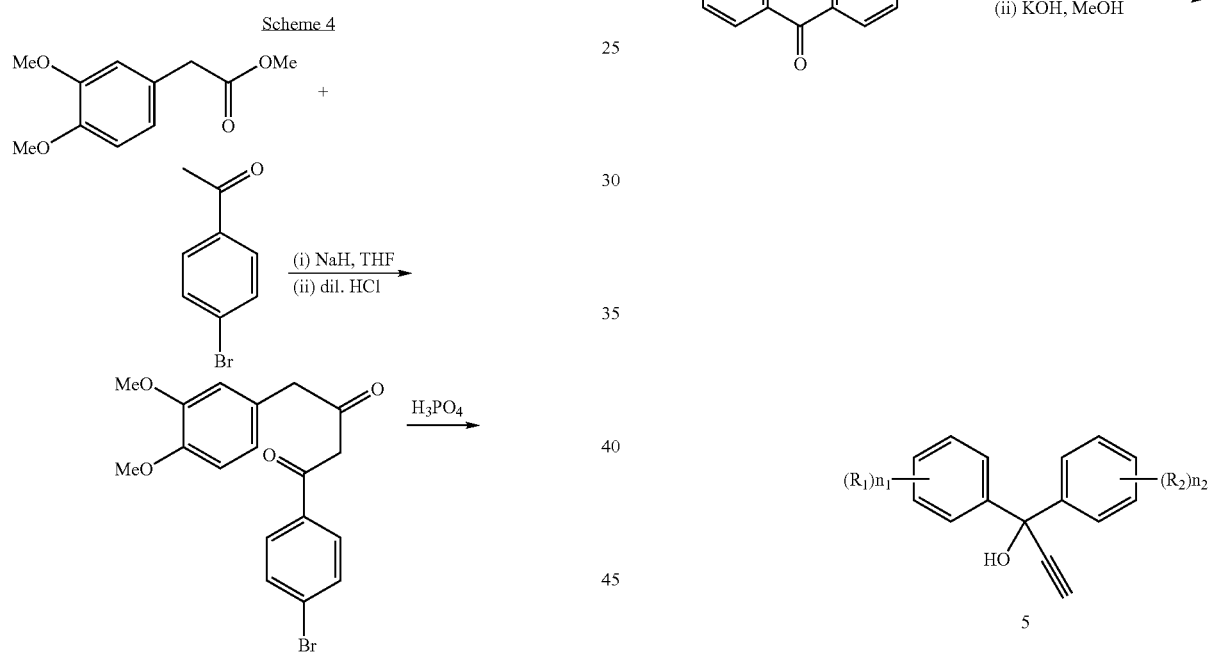
Scheme 5
Scheme 6
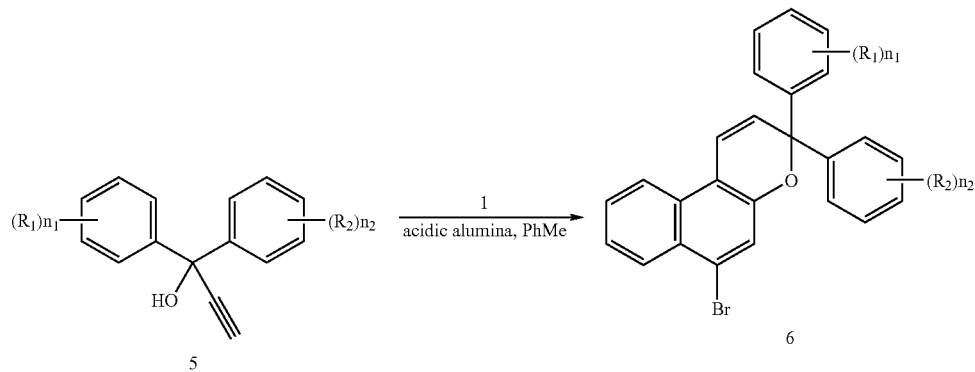

-continued
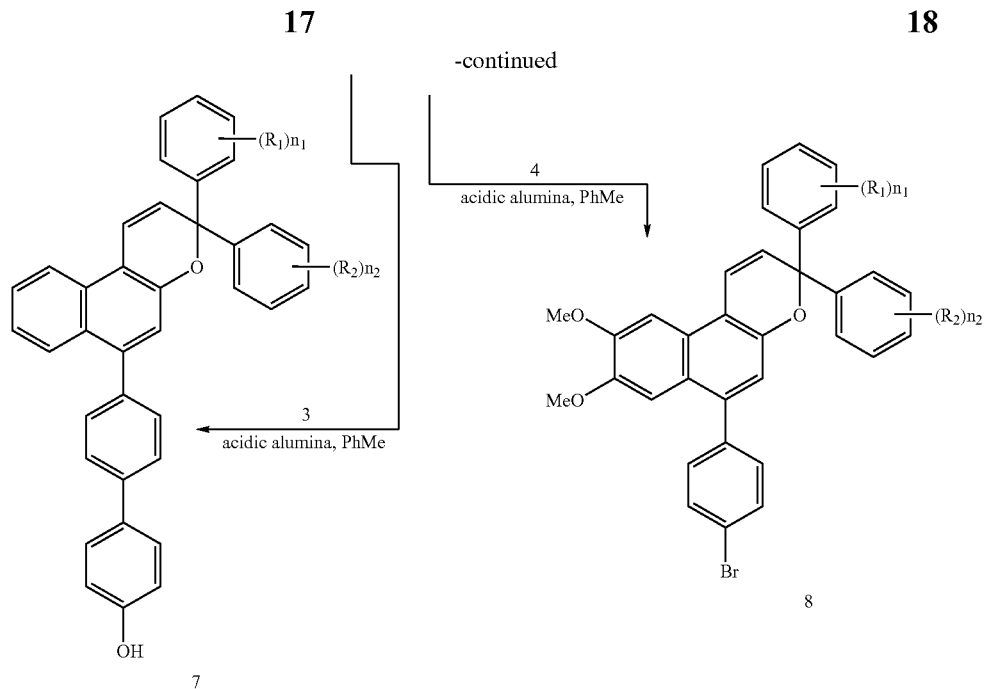
Scheme 7
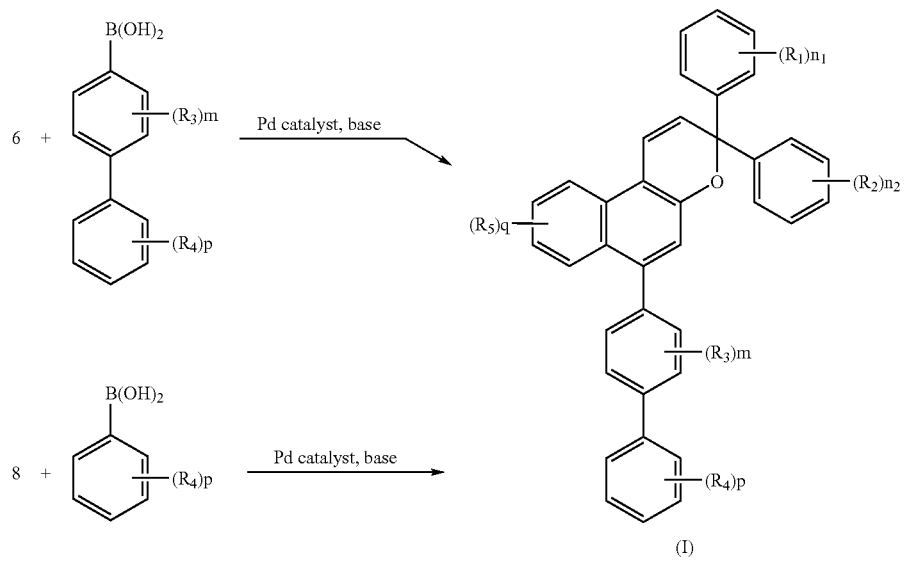

Scheme 8

[Chemical structures and reaction scheme showing naphthopyran synthesis with Pd(PPh₃)₄, Na₂CO₃, PhMe, EtOH, followed by (i) Bu₄NF, THF; (ii) C₁₂H₂₅I, K₂CO₃, Me₂CO]

The present invention also provides an optical article comprising one or more naphthopyran compounds (I) of the present invention. The naphthopyran compounds (I) of the present invention can be used in all kinds of optical devices and elements, such as ophthalmic elements and devices, display elements and devices, windows or mirrors. Non-limiting examples of ophthalmic elements include corrective and non-corrective lenses, including single vision or multi-vision lenses, which may be either segmented or non-segmented, as well as other elements used to correct, protect, or enhance vision, including without limitation contact lenses, intra-ocular lenses, magnifying lenses and protective lenses or visors. Non-limiting examples of display elements and devices include screens and monitors. Non-limiting examples of windows include automotive and aircraft transparencies, filters, shutters, and optical switches.

The optical article of the present invention is preferably a lens, and more preferably an ophthalmic lens.

When used in optical articles, the naphthopyran compounds may be incorporated, for example, in the bulk of a polymeric material of the optical article. Such a polymeric host material is generally a solid transparent or optically clear material. Preferred polymeric host materials are for example polymers of polyol(allyl carbonate) monomers, polyacrylates, poly(triethyleneglycol dimethacrylate), polyperfluoroacrylates, cellulose acetate, cellulose triacetate, cellulose acetate propionate, cellulose acetate butyrate, poly(vinyl acetate), poly(vinyl alcohol), polyurethanes, polycarbonates, poly(ethylene terephthalate), polystyrene, polyfluorostyrene, poly(diethylene glycol bis(alkyl carbonate)) and mixtures thereof.

The photochromic substances of the present invention may be incorporated into the polymeric host material by various methods described in the art. Such methods include dissolving or dispersing the photochromic substance within the host material by adding it to the monomeric host material prior to polymerization, or by imbibition of the photochromic substance into the host material by immersion of the host material in a hot solution of the photochromic substance.

In another preferred embodiment of the present invention the photochromic dyes are not incorporated into the bulk of an organic polymeric host material, but are incorporated into a surface coating or a film applied onto an optical substrate. The substrate is preferably a transparent or optically clear material, such as glass or organic polymers commonly used in optical applications.

The present invention of course also encompasses optical articles having at least one naphthopyran compound of formula (I) incorporated either in the bulk of the article, or in the coating of the article, or in the film applied onto the article. In one or more embodiments, the optical article includes a naphthopyran compound of formula (I) incorporated both into the bulk and into the coating of the article.

In still a more preferred embodiment of the present invention, the coating or film incorporating the photochromic naphthopyran compounds of the present invention is an anisotropic film or coating, i.e. it comprises a layer or medium which is able to function as an alignment layer for the dye molecules. Such an alignment layer may be for example an organic polymer, such as polyvinyl alcohol (PVA). One common method of aligning the molecules of a dichroic dye involves heating a sheet or layer of PVA to soften the PVA and then stretching the sheet to orient the polymer chains. The dichroic dye is then impregnated into the stretched sheet and dye molecules take the orientation of the polymer chains. Alternatively, the dichroic dye can be first impregnated into the PVA sheet, and thereafter the sheet can be heated and stretched as described above to orient the PVA polymer chains and associated dyes. In this manner, the molecules of the dichroic dye can be suitably positioned or arranged within the oriented polymer chains of the PVA sheet and a net linear polarization can be achieved.

In an even more preferred embodiment of the present invention, the novel naphthopyran compounds are not incorporated into a solid, isotropic or anisotropic host material, but into a fluid, mesomorphous or gel host medium. Dissolving or dispersing the naphthopyran compounds of the present invention in such a fluid, mesomorphous or gel host medium increases the coloration rate and even more drastically the fading rate. The recovery time, i.e. the time it takes the material to revert from an absorptive condition to a clear condition, can thus be reduced to less than 5 minutes.

The fluid or mesomorphous host medium incorporating at least one naphthopyran compound is preferably selected from the group consisting of organic solvents, liquid crystals, and mixtures thereof.

The naphthopyran compounds of the present invention are preferably dissolved in the host medium.

The organic solvents may be selected for example from the group consisting of benzene, toluene, methyl ethyl ketone, acetone, ethanol, tetrahydrofurfuryl alcohol, N-methylpyrrolidone, 2-methoxyethyl ether, xylene, cyclohexane, 3-methylcyclohexanone, ethyl acetate, ethyl phenylacetate, tetrahydrofuran, methanol, methyl propionate, ethylene glycol and mixtures thereof.

The liquid crystal medium that may be used in the present invention includes, without being limited to, such materials as nematic or chiral nematic media. Alternatively a polymeric liquid crystal medium can be used as the host material. These liquid crystal and polymeric liquid crystal media are generally used in combination with an organic solvent, for example one of the organic solvents mentioned above.

The mixture of a fluid, mesomorphous or gel host medium and at least one of the naphthopyran compounds of the present invention preferably is incorporated into a device containing a mechanism for holding the mixture in a mechanically stable environment.

Such a device is disclosed for example in U.S. Pat. No. 6,690,495 which is hereby specifically incorporated by reference herein. Such a device comprises a pair of opposed substrates having a gap therebetween for receiving the mixture of a fluid, mesomorphous or gel host medium and at least one photochromic dye of the present invention, and a frame for holding said pair of substrates adjacent one another.

An even more preferred device for holding the mixture in a mechanically stable environment is the one described in WO 2006/013250 and FR 2879757, which are hereby specifically incorporated by reference herein.

The preferred optical article of the present invention, disclosed in WO 2006/013250, comprises an optical component provided with at least one transparent cell arrangement juxtaposed in a parallel direction to the surface thereof, each cell being tightly closed and containing said fluid, mesomorphous or gel host medium and said at least one naphthopyran compound of the present invention. The transparent cell arrangement forms a layer whose height perpendicular to the component surface is less than 100 µm, preferably comprised between 1 µm and 50 µm.

The transparent cell arrangement may be formed either directly on a transparent rigid substrate of said optical component, or alternatively a transparent film incorporating the transparent cell arrangement may be applied on a transparent rigid substrate of the optical component.

The cell arrangement preferably occupies a large fraction of the total surface of the optical component. The ratio of the total surface occupied by the cells to the total surface of the optical component is preferably at least 90%, more preferable comprised between 90 and 99.5%, and most preferably between 96% and 98.5%.

The cell arrangement may be composed for example of hexagonal or rectangular cells, whose dimensions may be described by (a) their size parallel to the surface of the optical component, which is preferably of at least 1 µm, more preferably comprised between 5 µm and 100 µm;

(b) the height of the cells perpendicular to the component surface, which is preferably less than 100 µM, and is more preferably comprised between 1 µm and 50 µm; and (c) the thickness of the partitions separating the tightly closed cells from each other, which is preferable comprised between 0.10 and 5.00 µm.

EXAMPLES

Synthesis of Intermediate Compounds Used in the Synthesis of Example Compounds

3-Methoxynaphthalen-1-yl trifluoromethanesulfonate

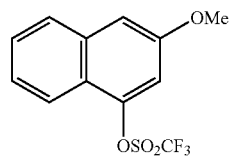

2

Trifluoromethanesulfonic anhydride (9.35 g, 32.8 mmol) was added dropwise to a solution of 3-methoxy-1-naphthol (5.77 g, 32.8 mmol) and $Et_3N$ (10 ml) in dichloromethane (100 ml) at 0° C. with stirring. After 1 h the resulting solution was washed with HCl (50 ml, 1 M) and saturated $Na_2CO_3$ (50 ml), dried ($MgSO_4$) and the solvent removed under reduced pressure. The residue was chromatographed on silica using EtOAc (7% in hexanes) to give the title compound (7.45 g, 74%) as a colourless oil.

3-Methoxy-1-(4'-methoxy-4-biphenyl)naphthalene

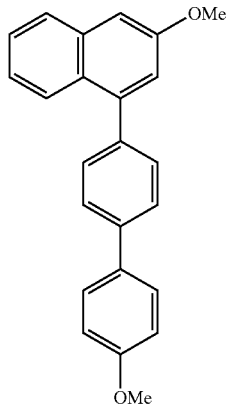 [SMILES: COc1ccc(-c2ccc(-c3cc(OC)cc4ccccc34)cc2)cc1]

A mixture of 3-methoxynaphthalen-1-yl trifluoromethanesulfonate (0.5 g, 1.7 mmol), (4'-methoxy-4-biphenyl)boronic acid (0.58 g, 2.5 mmol), Na$_2$CO$_3$ (0.27 g, 2.5 mmol) and Pd(PPh$_3$)$_4$ (40 mg, 2 mol %) in PhMe (20 ml) and EtOH (20 ml) under N$_2$ was heated at reflux. After 2 h the mixture was cooled, poured into water (100 ml), extracted with dichloromethane (3×50 ml), dried (MgSO$_4$) and the solvent removed under reduced pressure. The residue was dissolved in dichloromethane, filtered through a short plug of silica and the solvent removed under reduced pressure to give the title compound (0.44 g, 76%) as a colourless powder.

4-(4'-Hydroxy-4-biphenyl)-2-naphthol

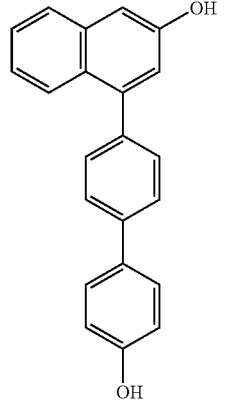

Boron tribromide (1.00 g, 3.9 mmol) was added dropwise to a solution of 3-methoxy-1-(4'-methoxy-4-biphenyl)naphthalene (0.44 g, 1.3 mmol) in dichloromethane (50 ml) at 0° C. under N$_2$. The solution was warmed to rt and stirring continued overnight, poured into water (200 ml), extracted with Et$_2$O (3×50 ml), dried (MgSO$_4$) and the solvent removed under reduced pressure to give the title compound (0.40 g, 100%) as a brown powder.

1-(4-Bromophenyl)-4-(3,4-dimethoxyphenyl)butane-1,3-dione

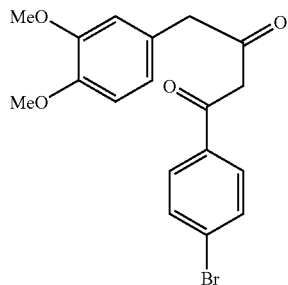 [SMILES: COc1ccc(CC(=O)CC(=O)c2ccc(Br)cc2)cc1OC]

Sodium hydride (60% dispersion, 3.80 g, 95.1 mmol) was added portionwise to methyl 2-(3,4-dimethoxyphenyl)acetate (10 g, 47.6 mmol) in Et$_2$O (100 ml) at 0° C. A solution of 4'-bromoacetophenone (9.48 g, 47.6 mmol) in Et$_2$O (50 ml) was added dropwise over 1 h. The mixture was heated at reflux for 16 h, cooled, poured into ice/HCl (2 M), extracted with Et$_2$O (3×100 ml), dried (MgSO$_4$) and the solvent removed under reduced pressure. The residue was crystallized from MeOH to give the title compound (9 g, 50%) as a tan powder.

4-(4-Bromophenyl)-6,7-dimethoxy-2-naphthol

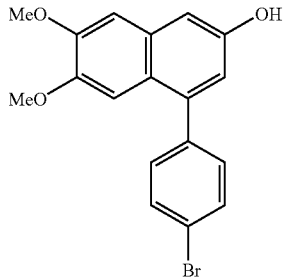

1-(4-Bromophenyl)-4-(3,4-dimethoxyphenyl)butane-1,3-dione (3 g, 8 mmol) in 85% phosphoric acid was heated at 70° C. for 20 h. The resulting solution was cooled, poured into water (150 ml) and filtered. The residue was dissolved in dichloromethane (50 ml), washed with water (50 ml), dried (MgSO$_4$) and the solvent was removed under reduced pressure to give the title compound (2.56 g, 90%) as a brown powder.

General Procedure for the Synthesis of 6-bromophenyl-8,9-dimethoxynaphtho[2,1-b]pyrans A mixture of 4-(4-bromophenyl)-6,7-dimethoxy-2-naphthol (9.7 mmol), 1,1-diarylprop-2-yn-1-ol (9.7 mmol) and acidic alumina (3 g) in toluene (100 ml) was heated at reflux. After 2 h the solution was filtered hot and the residue was washed with PhMe (50 ml). The solvent was removed under reduced pressure and the residue chromatographed on silica. The solvent was removed under reduced pressure and the residue was washed with MeOH to give the title compound which was purified by flash chromatography from silica gel. The following compounds were prepared in this way:

6-(4-Bromophenyl)-8,9-dimethoxy-3-phenyl-3-(4-piperidinophenyl)-3H-naphtho[2,1-b]pyran dichloromethane (70% in hexanes) as eluent, 69% as a purple powder

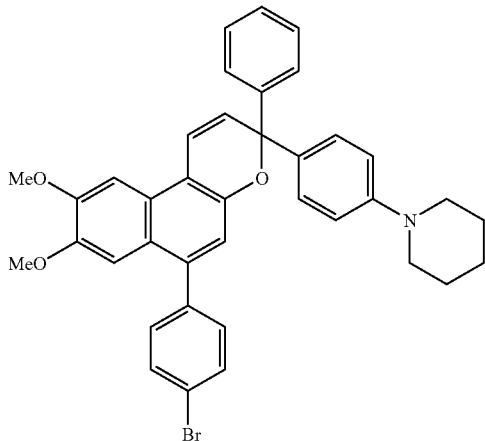 [SMILES: COc1cc2c(-c3ccc(Br)cc3)cc3c(c2cc1OC)C=CC(c1ccccc1)(c1ccc(N2CCCCC2)cc1)O3]

6-(4-Bromophenyl)-8,9-dimethoxy-3-phenyl-3-(4-pyrrolidinophenyl)-3H-napho[2,1-b]pyran dichloromethane as eluent, 64% as a violet powder

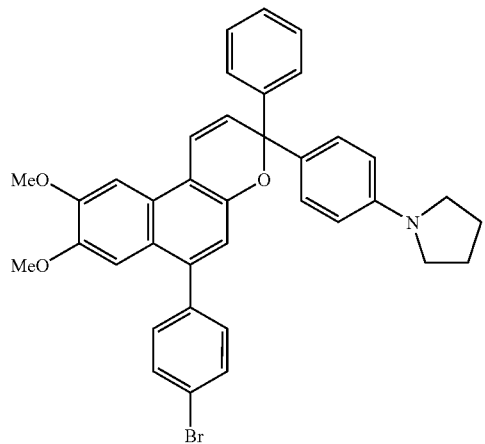 [SMILES: COc1cc2c(-c3ccc(Br)cc3)cc3c(c2cc1OC)C=CC(c1ccccc1)(c1ccc(N2CCCC2)cc1)O3]

6-(4-Bromophenyl)-8,9-dimethoxy-3-(4-butoxyphenyl)-3-(9-julolidinyl)-3H-naphtho[2,1-b]pyran dichloromethane as eluent, 51% as a green powder

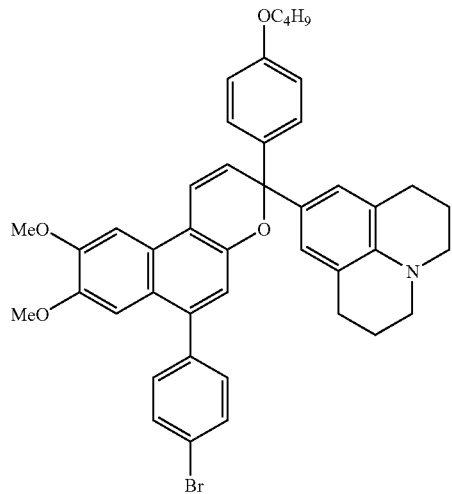

General Procedure for the Synthesis of 6-biphenylnaphtho[2,1-b]pyrans from 6-bromonaphthopyrans The appropriate 6-bromo-3H-naphtho[2,1-b]pyran (1 mmol) was dissolved in THF (10 ml) containing water (1 ml) under nitrogen and [1,1'-bis(diphenylphosphino)ferrocene] dichloro palladium(II) (1 mol %) was added. The solution was stirred for 5 min and potassium carbonate (1.1 mmol), potassium fluoride (3.3 mmol) and the appropriate 4'-substituted-4-biphenylboronic acid (1.1 mmol) were added. The reaction mixture was refluxed for 20 hours. Solvent was removed and the residue was flash chromatographed using petroleum ether-ethyl acetate (97-3) on silica gel. Recrystallisation from ethyl acetate and hexane gave the title compounds.

The following examples were prepared using the intermediate steps described hereinbefore in this way.

Example (a)

6-(4'-Pentyl-4-biphenyl)-3-phenyl-3-(4-piperidinophenyl)-3H-naphtho[2,1-b]pyran (m.p. 95-97° C.) from 6-bromo-3-(4-piperidinophenyl)-3H-naphtho[2,1-b]pyran and 4'-pentylbiphenyl-4-boronic acid.

Example (b)

6-(4'-Pentyl-4-biphenyl)-3-(4-methoxyphenyl)-3-(4-morpholinophenyl)-3H-naphtho[2,1-b]pyran: (m.p. 166-167° C.) from 6-bromo-3-(4-methoxyphenyl)-3-(4-morpholinophenyl)-3H-naphtho[2,1-b]pyran and 4'-pentylbiphenyl-4-boronic acid.

Example (c)

6-(4'-Pentyl-4-biphenyl)-3-phenyl-3-(4-pyrrolidinophenyl)-3H-naphtho[2,1-b]pyran: (m.p. 155-157° C.) from 6-bromo-3-phenyl-3-(4-pyrrolidinophenyl)-3H-naphtho[2,1-b]pyran and 4'-pentylbiphenyl-4-boronic acid.

Example (d)

6-(4'-Pentyl-4-biphenyl)-3-phenyl-3-(julolidin-9-yl)-3H-naphtho[2,1-b]pyran: (m.p. 130-132° C.) from 6-bromo-3-phenyl-3-(julolidin-9-yl)-3H-naphtho[2,1-b]pyran and 4'-pentylbiphenyl-4-boronic acid.

Example (e)

6-(4'-Pentyl-4-biphenyl)-3-(4-methoxyphenyl)-3-(julolidin-9-yl)-3H-naphtho[2,1-b]pyran: (m.p. 89° C.) from 6-bromo-3-(4-methoxyphenyl)-3-(julolidin-9-yl)-3H-naphtho[2,1-b]pyran and 4'-pentylbiphenyl-4-boronic acid.

Example (f)

6-(4'-Pentyl-4-biphenyl)-3-phenyl-3-(4-fluorophenyl)-3H-naphtho[2,1-b]pyran: (m.p. 55° C.) from 6-bromo-3-phenyl-3-(4-fluorophenyl)-3H-naphtho[2,1-b]pyran and 4'-pentylbiphenyl-4-boronic acid.

Example (g)

6-(4'-Butoxy-4-biphenyl)-3-phenyl-3-(4-pyrrolidinophenyl)-3H-naphtho[2,1-b]pyran: (m.p. 107° C.) from 6-bromo- 3-phenyl-3-(4-pyrrolidinophenyl)-3H-naphtho[2,1-b]pyran and 4'-butoxybiphenyl-4-boronic acid.

Example (h)

6-(4'-Hexyloxy-4-biphenyl)-3-phenyl-3-(4-pyrrolidinophenyl)-3H-naphtho[2,1-b]pyran: (m.p. 93° C.) from 6-bromo-3-phenyl-3-(4-pyrrolidinophenyl)-3H-naphtho[2,1-b]pyran and 4'-hexyloxybiphenyl-4-boronic acid.

Example (i)

6-(4'-Hexyloxy-4-biphenyl)-3-(4-fluorophenyl)-3-(4-pyrrolidinophenyl)-3H-naphtho[2,1-b]pyran: (m.p. 149° C.) from 6-bromo-3-(4-fluorophenyl)-3-(4-pyrrolidinophenyl)-3H-naphtho[2,1-b]pyran and 4'-hexyloxybiphenyl-4-boronic acid.

Example (j)

6-(4'-Pentyl-4-biphenyl)-3-(4-fluorophenyl)-3-(4-pyrrolidinophenyl)-3H-naphtho[2,1-b]pyran: (m.p. 153° C.) from 6-bromo-3-(4-fluorophenyl)-3-(4-pyrrolidinophenyl)-3H-naphtho[2,1-b]pyran and 4'-pentylbiphenyl-4-boronic acid.

General Procedure for the Synthesis of 6-biphenyl-8,9-dimethoxynaphtho[2,1-b]pyrans front 6-bromophenyl-8,9-dimethoxynaphthopyrans A mixture of the appropriate 6-bromophenyl-8,9-dimethoxynaphthopyran (2.4 mmol), and an arylboronic acid (3.6 mmol) in 1,2-dimethoxyethane (50 ml) was degassed by purging with nitrogen. Tetrakis(triphenylphosphine)palladium(0) (5 mol %) was added followed by $Na_2CO_3$ (7.2 mmol) in degassed water (50 ml). The mixture was heated at 100° C. for 16 h, cooled, poured into water, extracted with dichloromethane (5×50 ml), dried ($MgSO_4$) and the solvent removed under reduced pressure. The residue was chromatographed on silica. The solvent was removed under reduced pressure and the residue crystallised from acetone-methanol by slow evaporation to give the title compounds.

The following examples were prepared using the intermediate steps described hereinbefore in this way.

Example (m)

6-(4'-Hexyloxy-4-biphenyl)-8,9-dimethoxy-3-phenyl-3-(4-piperidino phenyl)-3H-naphtho[2,1-b]pyran dichloromethane as eluent, 72% as a purple powder, mp 198-199° C.

Example (n)

6-(4'-Dibutylamino-4-biphenyl)-8,9-dimethoxy-3-phenyl-3-(4-pyrrolidinophenyl)-3H-naphtho[2,1-b]pyran butanone (15% in cyclohexane) as eluent, 73% as a colourless powder, mp 174-175° C.

Example (o)

6-(4-(Hexyloxy-4-biphenyl)-8,9-dimethoxy-3-phenyl-3-(4-pyrrolidinophenyl)-3H-naphtho[2,1-b]pyran butanone (20% in cyclohexane) as eluent, 76% as a colourless powder, mp 197-198° C.

Example (p)

3-(4-Butoxyphenyl)-8,9-dimethoxy-6-(4'-hexyloxy-4-biphenyl)-3-(9-julolidinyl)-3H-naphtho[2,1-b]pyran acetone, butanone, cyclohexane (8:8:84) as eluent, 53% as a violet powder, mp 111-112° C.

8,9-Dimethoxy-3-phenyl-3-(4-pyrrolidinophenyl)-6-(4'-triisopropylsilyloxy-4-biphenyl)]-3H-naphtho[2,1-b]pyran dichloromethane as eluent, 70% as a colourless powder

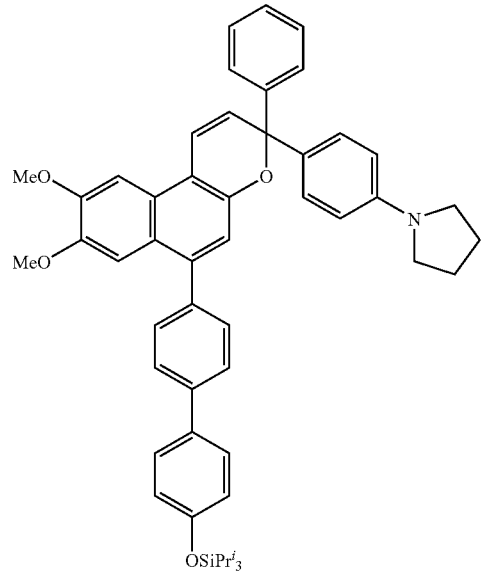

8,9-Dimethoxy-6-(4'-(hydroxy-4-biphenyl)-3-phenyl-3-(4-pyrrolidinophenyl)-3H-naphtho[2,1-b]pyran

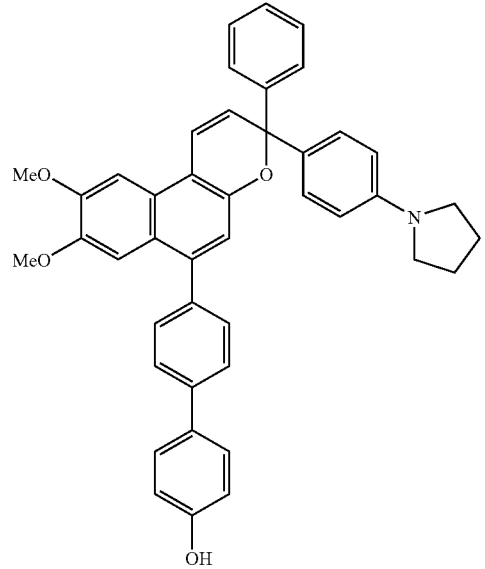 [SMILES: COc1cc2c(-c3ccc(-c4ccc(O)cc4)cc3)cc3c(c2cc1OC)C=CC(c1ccccc1)(c1ccc(N2CCCC2)cc1)O3]

A solution of tetrabutylanimonium fluoride (1M in THF) (1.26 mmol) was added to a solution of 8,9-dimethoxy-3-phenyl-3-(4-pyrrolidinophenyl)-6-(4'-triisopropylsilyloxy-4-biphenyl)-3H-naphtho[2,1-b]pyran (1.26 mmol) in THF (30 ml) with stirring. After 5 min HCl (3 ml, 1 M) was added and the solvent removed under reduced pressure. The residue was chromatographed on silica using dichloromethane (70% in hexanes) as eluent The solvent was removed under reduced pressure and the residue crystallised from acetone/MeOH to give the title compound (57%) as a cream powder, mp 154-155° C.

Example (l)

8,9-Dimethoxy-6-(4'-dodecyloxy-4-biphenyl)-3-phenyl-3-(4-pyrrolidinophenyl)-3H-naphtho[2,1-b]pyran To a solution of 8,9-dimethoxy-6-(4'-hydroxy-4-biphenyl)-3-phenyl-3-(4-pyrrolidinophenyl)-3H-naphtho[2,1-b]pyran (0.63 g, 1.0 mmol) and 1-iododecane (0.59 g, 2.0 mmol) in acetone (50 ml) was added potassium carbonate (1.38 g, 10 mmol) and the mixture refluxed for 6 h. After this time the mixture was poured into water and extracted with dichloromethane (3×50 ml). The extracts were dried and evaporated and the residue triturated with acetone to provide the title compound (70%) as a colourless powder, mp 173-175° C.

Example (k)

6-(4'-Dodecyloxy-4-biphenyl)-3-(4-hexyloxyphenyl)-3-[4-(4-methylpiperidino)phenyl]-3H-naphtho[2,1-b]pyran To a solution of 6-(4'-hydroxy-4-biphenyl)-3-[4-(hexyloxy)phenyl]-3-[4-(4-methylpiperidino)phenyl]-3H-naphtho[2,1-b]pyran (0.73 g, 1.0 mmol) and 1-iododecane (0.59 g, 2.0 mmol) in acetone (50 ml) was added potassium carbonate (0.72 g, 5 mmol) and the mixture refluxed for 24 h. After this time the mixture was poured into water and extracted with dichloromethane (3×50 ml). The extracts were dried and evaporated and the residue filtered through a short plug of silica using 60% dichloromethane in hexanes as eluent. The solvent was removed and the residue crystallised from acetone-methanol to give the title compound (0.81 g, 89%) as a pink powder, mp 45° C.

The invention claimed is:
1. A naphthopyran compound represented by the formula (I):

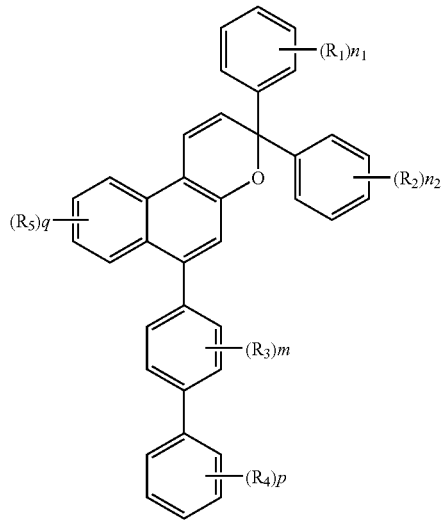

wherein:
$n_1$ is an integer comprised from 0 to 5 inclusive;
$n_2$ is an integer comprised from 0 to 5 inclusive;
p is an integer comprised from 0 to 5 inclusive;
m is an integer comprised from 0 to 4 inclusive;
q is an integer comprised from 0 to 5 inclusive;
$R_1$ and $R_2$, identical or different, independently from each other, a group halogen, —$R_a$, —OH, —$OR_a$, —SH, —$NH_2$, —$NR_aR_{a1}$, —$NR_bR_c$, —CO—$R_a$, —O—CO—$R^a$ and —$CO_2R_{a1}$, wherein:
$R_a$ is a linear or branched ($C_1$-$C_{18}$) alkyl group or a linear or branched ($C_1$-$C_{18}$) perfluoroalkyl group;
$R_{a1}$ is a hydrogen, linear or branched ($C_1$-$C_{18}$) alkyl group and linear or branched ($C_1$-$C_{18}$) perfluoroalkyl group;
wherein $R_b$ and $R_c$,
together and in combination with the nitrogen atom, represent a saturated 5 to 7 membered heterocyclic group which comprises optionally one additional heteroatom selected from O, N or S, and which may be optionally substituted by a halogen, $R_a$, —OH, —$OR_a$, —$NH_2$, or —$NR_aR_{a1}$, wherein $R_a$ and $R_{a1}$ are as defined hereinbefore;
or together and in combination with the nitrogen atom and the adjacent phenyl group form a heterocyclic group of formula (A):

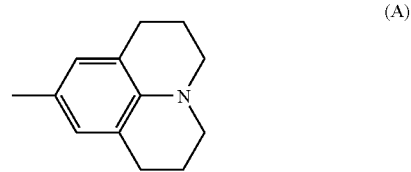

$R_3$ is a halogen, —$R_a$, —OH, —$OR_a$, —SH, —$SR_a$, —$NH_2$, and $NR_aR_{a1}$, wherein $R_a$ and $R_{a1}$ are as defined hereinbefore;
$R_4$ is a halogen, —$R_a$, —OH, —$OR_a$, —SH, —$SR_a$, —$NH_2$, —$NR_aR_{a1}$, —CO—$R_a$, or —$CO_2R_{a1}$, located at the para-position of the phenyl group, wherein $R_a$ and $R_{a1}$ are as defined hereinbefore;
$R_5$ is;
a halogen, —$R_a$, —OH, —$OR_a$, —SH, —$SR_a$, —$NH_2$, or —$NR_aR_{a1}$, wherein $R_a$ and $R_{a1}$ are as defined hereinbefore,
or when q is equal to 2 and then two $R_5$ substituents are located onto two adjacent carbon atoms selected from C-7, C-8, C-9 and C-10 of the naphtho[2,1-b]pyran group, they may further represent together a group —O—$(CH_2)_{q1}$—O— wherein q1 represents an integer comprised from 1 to 3 inclusive.
2. The naphthopyran compound according to claim 1, wherein:
$n_1$ is equal to 0 or 1, and $R_1$ is a halogen, —OH or —$OR_a$ located at the para- or ortho-position of the phenyl group;
$n_2$ is equal to 1 and $R_2$ is a halogen, —OH, —$OR_a$, or —$NR_bR_c$ located at the para-position of the phenyl group, wherein $R_a$, $R_b$ and $R_c$ are as defined hereinbefore;
m is equal to zero;
p is equal to 1 and $R_4$ is —$R_a$, —$OR_a$, or —$NR_aR_{a1}$; and
q is an integer comprised from 0 to 2 inclusive, and $R_5$ is —OH or —$OR_a$ located on the C-8 and/or C-9 of the naphtho[2,1-b]-pyran group.

3. The naphthopyran compound of claim 1, which is selected from one of the following compounds:
- 6-(4-Pentyl-4-biphenyl)-3-phenyl-3-(4-piperidinophenyl)-3H-naphtho[2,1-b]pyran;
- 6-(4-Pentyl-4-biphenyl)-3-(4-methoxyphenyl)-3-(4-morpholinophenyl)-3H-naphtho[2,1-b]pyran;
- 6-(4-Pentyl-4-biphenyl)-3-phenyl-3-(4-pyrrolidinophenyl)-3H-naphtho[2,1-b]pyran;
- 6-(4-Pentyl-4-biphenyl)-3-phenyl-3-(julolidin-9-yl)-3H-naphtho[2,1-b]pyran;
- 6-(4-Pentyl-4-biphenyl)-3-(4-methoxyphenyl)1-3-(julolidin-9-yl)-3H-naphtho[2,1-b]pyran;
- 6-(4-Pentyl-4-biphenyl)-3-phenyl-3-(4-fluorophenyl)-3H-naphtho[2,1-b]pyran;
- 6-(4-Butoxy-4-biphenyl)-3-phenyl-3-(4-pyrrolidinophenyl)-3H-naphtho[2,1-b]pyran;
- 6-(4-Hexyloxy-4-biphenyl)-3-phenyl-3-(4-pyrrolidinophenyl)-3H-naphtho[2,1-b]pyran;
- 6-(4-Hexyloxy-4-biphenyl)-3-(4-fluorophenyl)-3-(4-pyrrolidinophenyl)-3H-naphtho[2,1-b]pyran;
- 6-(4-Pentyl-4-biphenyl)-3-(4-fluorophenyl)-3-(4-pyrrolidinophenyl)-3H-naphtho[2,1-b]pyran;
- 6-(4-Hexyloxy-4-biphenyl)-8,9-dimethoxy-3-phenyl-3-(4-piperidinophenyl)-3H-naphtho[2,1-b]pyran;
- 6-(4'-(Dibutylamino)-4-biphenyl)-8,9-dimethoxy-3-phenyl-3-(4-pyrrolidinophenyl)-3H-naphtho[2,1-b]pyran;
- 6-(4-Hexyloxy-4-biphenyl)-8,9-dimethoxy-3-phenyl-3-(4-pyrrolidinophenyl)-3H-naphtho[2,1-b]pyran;
- 3-(4-Butoxyphenyl)-8,9-dimethoxy-6-(4'-hexyloxy-4-biphenyl)-3-(9-julolidinyl)-3H-naphtho[2,1-b]pyran;
- 8,9-Dimethoxy-6-(4'-dodecyloxy)-4-biphenyl)-3-phenyl-3-(4-pyrrolidinophenyl)-3H-naphtho[2,1-b]pyran; and
- 8,9-Dimethoxy-6-(4'-dodecyloxy-4-biphenyl)-3-(4-hexyloxyphenyl)-3-[4-(4-methylpiperidino)phenyl]-3H-naphtho[2,1-b]pyran.

4. An optical article comprising at least one naphthopyran compound according to claim 1.

5. The optical article according to claim 4, wherein the article further comprises a polymeric host material, the at least one naphthopyran compound being incorporated in the bulk of said polymeric host material.

6. The optical article according to claim 5, wherein the polymeric host material is selected from polymers of polyol (allyl carbonate) monomers, polyacrylates, poly(triethyleneglycol dimethacrylate), polyperfluoroacrylates, cellulose acetate, cellulose triacetate, cellulose acetate propionate, cellulose acetate butyrate, poly(vinyl acetate), poly(vinyl alcohol), polyurethanes, polycarbonates, poly(ethylene terephthalate), polystyrene), polyfluorostyrene, poly(diethylene glycol bis(alkyl carbonate)) or mixtures thereof.

7. The optical article according to claim 4, wherein the article comprises an optical substrate and at least one film or coating comprising the at least one naphthopyran compound.

8. The optical article according to claim 7, wherein the at least one film or coating is a dichroic film or coating comprising an anisotropic oriented polymer layer and the at least one naphthopyran compound.

9. The optical article according to claim 4, wherein the article further comprises a host medium selected from a fluid host medium, a mesomorphous host medium, a gel host medium, or a mixture of a fluid, mesomorphous or gel host medium, wherein the at least one naphthopyran compound is dissolved or dispersed within the host medium.

10. The optical article according to claim 9, wherein the host medium incorporating the at least one naphthopyran compound is selected from the group consisting of organic solvents, liquid crystals, liquid crystal polymers and mixtures thereof.

11. The optical article according to claim 9, wherein the article comprises a device that includes a mechanism for holding the host medium incorporating the at least one naphthopyran compound in a mechanically stable environment.

12. The optical article according to claim 11, wherein the device comprises a pair of opposed substrates having a gap there between for receiving the host medium and the at least one photochromic dye, and a frame for holding said pair of substrates adjacent one another.

13. The optical article according to claim 11, wherein the device comprises an optical component provided with at least one transparent cell arrangement juxtaposed in a parallel direction to the surface thereof, each cell being tightly closed and containing said host medium and said at least one naphthopyran compound.

14. The optical article according to claim 13, wherein the transparent cell arrangement forms a layer whose height perpendicular to the optical component surface is less than 100 µm.

15. The optical article according to claim 13, wherein the optical component comprises a transparent rigid substrate on which the transparent cell arrangement is formed.

16. The optical article according to claim 13, wherein the optical component comprises a transparent rigid substrate and, applied on said substrate, a transparent film incorporating the transparent cell arrangement.

17. The optical article according to claim 13, wherein the total surface occupied by the transparent cell arrangement comprises 90% or more of the total surface of the optical component.

18. The optical article according to claim 13 wherein each cell in the transparent cell arrangement has a height of at least 1 µm.

19. The optical article according to claim 13, wherein the cells in the transparent cell arrangement are separated from each other by means of partitions having a thickness of 0.10 to 5.00 µM.

20. The optical article according to claim 13, wherein the article is selected from the group consisting of ophthalmic elements, ophthalmic devices, display elements, display devices, windows, mirrors, lenses, and ophthalmic lenses.

* * * * *